United States Patent [19]

Ballantine et al.

[11] 4,014,862
[45] Mar. 29, 1977

[54] PRODUCTION OF HARDENED GELATIN LAYERS BY THE ADDITION OF QUATERNARY CARBAMOYL PYRIDINIUM COMPOUNDS

[75] Inventors: John Douglas Ballantine; Norman Alfred Smith, both of Ilford, England

[73] Assignee: Ilford Limited, Ilford, England

[22] Filed: July 6, 1973

[21] Appl. No.: 377,139

[30] Foreign Application Priority Data

July 12, 1972 United Kingdom ............ 32491/72

[52] U.S. Cl. .............................. 260/117; 96/111; 106/125
[51] Int. Cl.$^2$ ...................................... C09H 5/00
[58] Field of Search ................. 260/117; 96/111; 106/125

[56] References Cited

UNITED STATES PATENTS

| | | | |
|---|---|---|---|
| 1,981,292 | 11/1934 | Todd et al. | 260/117 UX |
| 3,511,849 | 5/1970 | Wilson | 260/117 X |
| 3,576,813 | 4/1971 | Burness et al. | 96/111 |
| 3,880,665 | 4/1975 | Himmelmann | 96/111 |

*Primary Examiner*—Eugene C. Rzucidlo
*Attorney, Agent, or Firm*—Wenderoth, Lind & Ponack

[57] ABSTRACT

The present invention relates to the production of hardened gelatin layers by means of quaternary carbamoyl pyridinium compounds. Preferably this method is used for the hardening of silver halide photographic material.

5 Claims, No Drawings

PRODUCTION OF HARDENED GELATIN LAYERS BY THE ADDITION OF QUATERNARY CARBAMOYL PYRIDINIUM COMPOUNDS

According to the present invention there is provided a method of producing a hardened gelatin layer which comprises treating an aqueous gelatin solution with an aqueous solution of a compound of the formula

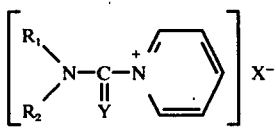

wherein $X^-$ is an anion, Y is a sulphur or an oxygen atom, $R_1$ and $R_2$ are each a lower alkyl group or an aryl group which is optionally substituted or taken together they form with the nitrogen atom a non-aromatic ring system, which is optionally substituted, the pyridinium nucleus also being optionally substituted, and then coating the gelatin solution as a layer on a base.

The method of the present invention finds particular use as a step in the preparation of photographic silver halide materials, and according to a preferred embodiment of the present invention, in a process for the production of a gelatino silver halide photographic material there is provided the step of treating an aqueous gelatino silver halide emulsion with an aqueous solution of a compound of formula I and then coating the aqueous emulsion as a layer onto a photobase.

By lower alkyl group is meant an alkyl group containing from 1–6, preferably 1–4 carbon atoms. Examples of lower alkyl groups are methyl, ethyl and isopropyl. An example of an aryl group is phenyl. Examples of substituents which may be present in the aryl groups are halogen atoms, nitro and lower alkyl groups.

Examples of anions are chloride, perchlorate and fluoroborate. The preferred anions, in as much as they render the compounds more stable, are perchlorate and fluoroborate.

Examples of substituents which may be present in the pyridinium nucleus are lower alkyl groups, in particular methyl groups, and amino groups. There may be up to four substituent groups on the pyridinium nucleus.

An example of a non-aromatic ring which may be formed by $R_1$ and $R_2$ taken together with the nitrogen atom is a morpholino ring or a piperidino ring.

A particularly preferred class of N,N-carbamoyl-pyridinium compounds for use in the present invention are those wherein the pyridinium nucleus is unsubstituted and one of $R_1$ and $R_2$ is an unsubstituted phenyl group and the other of $R_1$ and $R_2$ is a lower alkyl group.

A preferred class of compounds of formula I for use in the present invention are N,N-carbamoylpyridinium compounds wherein the pyridinium nucleus is unsubstituted and each of $R_1$ and $R_2$ is either an unsubstituted phenyl group or a lower alkyl group.

Further preferred classes of compounds of the formula I are those of the formulae

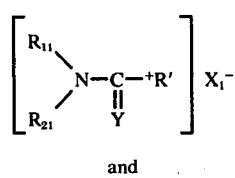

and

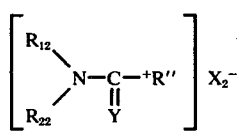

wherein
$R_{11}$ and $R_{21}$, independently from one another, represent a phenyl or a lower (up to 4 carbon atoms) alkyl group or, together with the nitrogen atom, a morpholino or piperidino radical, $R_{12}$ and $R_{22}$, independently from one another, represent a phenyl, a methyl or an isopropyl radical or, together with the nitrogen atom a piperidino radical, $^+R'$ represents a pyridinium radical which is bound by its ring nitrogen atom to —Cy— group and which carries no further substituents or up to three lower alkyl groups or an amino group, which amino group may be a primary, a secondary or a tertiary amino group, for instance a dimethylamino group.

$^+R''$ represents a pyridinium radical which is bound by its ring nitrogen atom to —CY— and which carries no further substituents or up to three methyl groups or a primary amino group or a dialkylamino group, $X_1^-$ represents a chloride, perchlorate or fluoroborate anion, $X_2^-$ represents a chloride or perchlorate anion, Y represents a sulphur or an oxygen atom, preferably an oxygen atom.

Preferably from 0.05 g to 10 g of the compound of formula I per 100 g of gelatin in the solution are used in the method of the present invention.

The N,N-carbamoylpyridinium compounds of formula I may be prepared via the intermediate carbamoyl chlorides. The intermediate carbamoyl chlorides may be prepared from the appropriate amine and phosgene as described by T. W. Price J.C.S. 1926, 3230.

The following procedure illustrates the production of phenyl isopropyl carbamoyl pyridinium chloride (Compound 6) via phenyl isopropyl carbamoyl chloride.

PROCEDURE

Phenyl Isopropyl Carbamoyl Chloride

A solution of N-isopropylaniline (30 g) in dry benzene (150 ml) was cooled to 5°–10° C and phosgene passed therethrough slowly for 1½ hours. The mixture was refluxed for 1 hour to remove excess phosgene, cooled and the amine hydrochloride was filtered off. The solvent was evaporated and the residue recrystallised from benzene-petroleum ether 1:1, giving 21.6 g, m.p. 89°–90° C.

Phenyl Isopropyl Carbamoyl Pyridinium Chloride

This compound was prepared from the phenyl isopropyl carbamoyl chloride prepared above as follows:

Phenyl isopropyl carbamoyl chloride (5 g) was dissolved in pyridine at room temperature. The solution was allowed to stand for 3 hours and was left overnight at 0° C. The solid material was filtered off, washed well with ether and dried, yielding 6.0 g material m.p. 114°–117° C.

The perchlorates and fluoroborates were prepared from the pyridinium chlorides in a manner known per se.

The compounds of formula I wherein $R_1$ and $R_2$ taken together with N form a non-aromatic ring system may be prepared similarly using the appropriate chloride prepared from the heterocyclic amine and phosgene which is then reacted with a pyridine.

The compounds of formula I wherein Y is a sulphur atom may be prepared similarly via the thio-carbamoyl chloride and then reacted with a pyridine.

The following compounds of formula I were prepared and tested in the example which follows:

Compound 1 = diphenyl carbamoyl pyridinium chloride

Compound 2 = diphenyl carbamoyl-2-aminopyridinium chloride

Compound 3 = diphenyl carbamoyl-3-aminopyridinium perchlorate

Compound 4 = methyl phenyl carbamoyl pyridinium chloride

Compound 5 = dimethyl carbamoyl pyridinium chloride

Compound 6 = phenyl isopropyl carbamoyl pyridinium chloride

Compound 7 = diphenylcarbamoyl-2,4,6, trimethyl-pyridinium chloride

Compound 8 = methylphenylcarbamoyl-4 dimethylaminopyridinium chloride

Compound 9 = piperidinocarbonyl pyridinium perchlorate

Compound 10 = dimethylthiocarbamoyl pyridinium perchlorate.

EXAMPLE

The compounds were tested by the scratch resistance method. This involves drawing a loaded stylus across a swollen gelatin layer, and determining the minimum weight required to scratch the surface.

The aqueous gelatin coating solutions were made up as follows:

17.5 g of gelatin were soaked in 150 ml of water for 20 minutes and melted out at 60° for 10 minutes. The pH of this gelatin solution was adjusted to 6.5. Test compound (Nos. 1 to 10), 0.00125 moles, was dissolved in ethanol 25 ml/water 35 ml, and added to the gelatin solution. The pH of the gelatin solution was readjusted to 6.5 and the volume as made up to 250 mls with water; 200μ thick coatings were made with a doctor bar on film base and dried in a fan-assisted drying cabinet without heat.

The coatings were kept at 22° C, 50% RH and 43° C, 69% RH. Scratch measurements were made after 20 minutes soaking in water at 20° C.

The results obtained are shown in the accompanying Table.

Table

| Compound | pH | After 3 hrs. | 2 days 22° C, 50% RH | 2 days 43° C, 69% RH | 7 days 22° C, 50% RH | 7 days 43° C, 69% RH |
|---|---|---|---|---|---|---|
| Control | 6.5 | 30 g | 30 g | 30 g | 35 g | 40 g |
| 1 | 6.5 | 225 g | 230 g | 215 g | 175 g | 295 g |
| 2 | 6.5 | 40 g | 90 g | 400 g | 150 g | 410 g |
| 3 | 6.5 | 145 g | 200 g | 270 g | 150 g | 295 g |
| 4 | 6.5 | 550 g | 600 g | 740 g | 720 g | 700 g |
| 5 | 6.5 | 640 g | 570 g | 580 g | 730 g | 640 g |
| 6 | 6.5 | 240 g | 600 g | 830 g | 550 g | 835 g |
| 7 | 6.5 | 140 g | 150 g | 200 g | 220 g | 205 g |
| 8 | 6.5 | 30 g | 75 g | 340 g | 105 g | 340 g |
| 9 | 6.5 | 570 g | 610 g | 700 g | 630 g | 650 g |
| 10 | 6.5 | 85 g | 420 g | 700 g | 600 g | 710 g |

We claim:

1. A method of producing a hardened gelatin layer which comprises treating an aqueous gelatin solution with an aqueous solution of a hardening agent of the formula

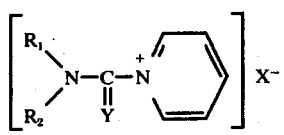

wherein $X^-$ is a perchlorate or fluoroborate anion, Y is an oxygen atom, $R_1$ and $R_2$ are each a lower alkyl or aryl group which is optionally substituted, or $R_1$ and $R_2$ taken together with the nitrogen atom form a non-aromatic ring system, which is optionally substituted, the pyridinium nucleus being unsubstituted or substituted by 1 to 4 members selected from the group consisting of lower alkyl and amino, and coating the resultant gelatin solution as a layer on a base.

2. A method according to claim 1, wherein the hardening agent of formula I is one in which Y is an oxygen atom, each of $R_1$ and $R_2$ is an unsubstituted phenyl group or a lower alkyl group and the pyridinium nucleus is unsubstituted.

3. A method according to claim 1 wherein the hardening agent of formula I is one in which Y is an oxygen atom, $R_1$ is a phenyl group, $R_2$ is a lower alkyl group and the pyridinium nucleus is unsubstituted.

4. A method according to claim 1, wherein the hardening agent is utilized in a quantity of from 0.05 to 10 g per 100 g of the gelatin present in the aqueous gelatin solution.

5. A method according to claim 1, wherein the hardening agent is diphenyl carbamoyl-3-aminopyridinum perchlorate.

* * * * *